United States Patent [19]

Heenan

[11] Patent Number: 4,505,590
[45] Date of Patent: Mar. 19, 1985

[54] MOBILE TESTING APPARATUS

[75] Inventor: Sidney A. Heenan, Park Ridge, Ill.

[73] Assignee: Amerace Corporation, New York, N.Y.

[21] Appl. No.: 455,297

[22] Filed: Jan. 3, 1983

Related U.S. Application Data

[63] Continuation-in-part of Ser. No. 412,911, Aug. 30, 1982, abandoned.

[51] Int. Cl.$^3$ .............................................. G01N 21/55
[52] U.S. Cl. ................................................. 356/445
[58] Field of Search ................ 356/445, 446, 447, 448

[56] References Cited

U.S. PATENT DOCUMENTS

| T987,003 | 10/1979 | Johnson et al. | 356/447 |
| 3,332,327 | 7/1967 | Heenan | 350/103 |
| 4,373,819 | 2/1983 | Pallotta | 356/445 |

*Primary Examiner*—R. A. Rosenberger
*Attorney, Agent, or Firm*—David Teschner; Ronald A. Sandler

[57] ABSTRACT

A mobile apparatus for detecting reflectivity of markers on a roadway surface is disclosed. The apparatus includes a vehicle and an elongated shroud assembly which has mounted therein a light source for directing light toward a marker and a light receptor for detecting light reflected from the marker, as the apparatus moves along the roadway surface. An aperture housing is mounted to the shroud and light directed to and reflected from the marker must pass through the aperture housing. In one embodiment the shroud is pivotally connected at one end to the vehicle and positioning means are provided for maintaining that portion of the shroud which will normally overlie the marker when light is reflected therefrom at a uniform and preselected height from the roadway surface. In another embodiment, the shroud is rigidly fixed to the vehicle, but the aperture is constructed to "float" at a uniform and preselected height from the roadway surface. By so uniformly positioning the aperture housing or a point on the shroud, the length of the light path from the source to the marker and back to the receptor is maintained substantially constant, regardless of vertical movement of the light source relative to the roadway surface due to bouncing, irregular road surfaces, etc.

16 Claims, 13 Drawing Figures

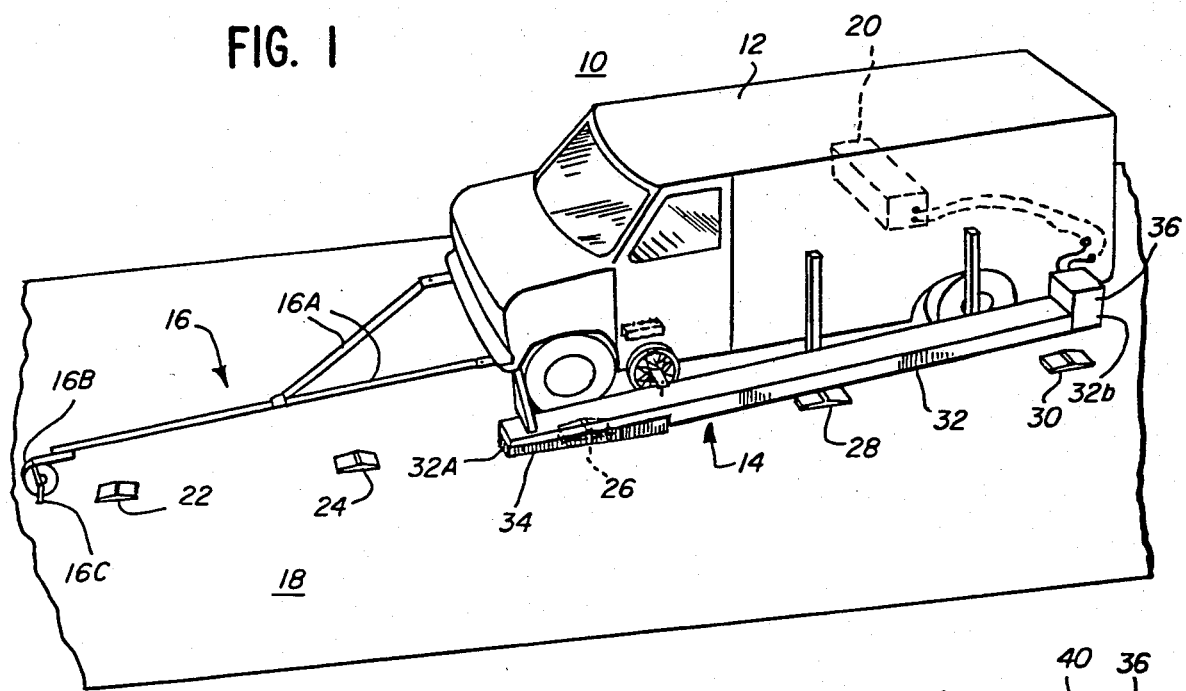
FIG. 1
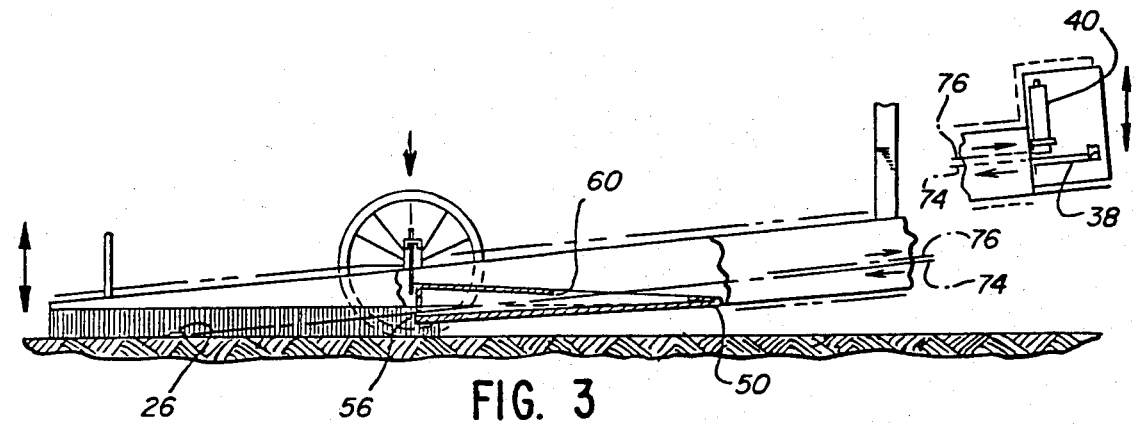
FIG. 2
FIG. 3

MOBILE TESTING APPARATUS

RELATED APPLICATION

This application is a continuation-in-part of application, Ser. No. 412,911 filed Aug. 30, 1982 now abandoned.

BACKGROUND OF THE INVENTION

This invention relates to a mobile apparatus for continuous on-site testing and measuring of the reflectance of retroreflective roadway markers and other reflective materials such as painted and applied reflective striping materials.

Retroreflective pavement markers of the type disclosed in U.S. Pat. No. 3,332,327 are commonly used to delineate road edges and lanes and to provide other information to vehicle operators. The effectiveness of such pavement markers, as with other reflective materials, diminishes with use and weathering so that their reflectance decreases in time.

Specific roadway, traffic and other conditions also affect groups of markers on the same highway differently, and some groups of the markers may need replacement at different time intervals than others. Today, testing of the effectiveness of roadway pavement markers generally is accomplished by visual inspection, or, on a very limited basis, removing markers from the roadway for off-site testing at a lab facility. Moreover, lane-striping materials and painted lines are tested by stationary photometers which are positioned over the stripes, or by simple visual observation. Neither of these is an efficient way of determining the reflective qualities of those items for replacement purposes.

It therefore is a primary object of this invention to provide a mobile test apparatus for continuous on-site testing of the reflectance of pavement markers, reflective striping and the like.

Another primary object of the invention is to provide a mobile test apparatus for effective on-site testing of the reflectance of markers or the like which is capable of conducting such testing while moving along with traffic on the roadway, thereby to enable the testing to be conducted with a minimum of interruption of traffic flow and under substantially safe conditions.

It is a further object of the invention to provide a mobile testing apparatus which also will render an effective accurate record of the reflectance of all markers tested, so that, if desirable, only selected units may be replaced, depending upon the precise location of the defective units or the ineffective reflective or other striping materials.

Presently markers are laboratory tested according to standardized methods using a darkened room or tunnel in which a light source is directed at a reflector and the reflected light is received by a receptor. The distance from the source to the reflector and the reflector to the receptor is accurately controlled, as is the angular relationship between the incident and reflected light beams. Any changes in these distances and/or angles will substantially change the measured value of the reflected light and thus the determination of the unit's reflectance.

In any mobile testing apparatus it is also necessary to accurately control the source/marker-marker/receptor distances and angular relationships. For example, a mere two-inch vertical movement during operation of a movable test vehicle could result in a change in light path length which results in over a 50 percent error in the measured reflectance.

Prior attempts to provide mobile testing apparatus have not controlled such distances and angular relationships which change due to the movement and bouncing of the vehicle, and/or vertical curvature of the road. Thus, in prior devices, even though the marker may have been within desirable limits, the test apparatus could indicate an ineffective marker solely due to the changes in light path length. One prior device used "chopped light" for daytime testing and another used a shroud and is referred to as the "IRMA" device. One or more of these devices have other deficiencies such as a wide observation angle effect, graphic data display, and lack of control of test distance as the vehicle moved.

It is therefore another primary object of this invention to provide a test apparatus in which the length of the light path is maintained substantially uniform even though the testing vehicle, and thus light source, may move vertically relative to the roadway surface.

These and other objects of this invention will become apparent from the following description and appended claims.

SUMMARY OF THE INVENTION

The invention provides a mobile reflectance testing apparatus which employs a light-shielded shroud for movement over and for enclosing a marker, a light source for directing the light along the shroud to the marker and a receptor for receiving the reflected light. Data processing means is provided for analyzing reflected light for reflectance and comparing the actual reflectance to a standard unit.

In one embodiment, a floating aperture assembly is provided in the shroud between (1) the source and receptor and (2) the marker to maintain a substantially uniform light path and thus minimize variations in reported values of reflectance due to variations in light path length. In use, the floating aperture is maintained at a uniform and preselected distance from the roadway surface so that vertical movement of the vehicle and the source and receptor have little, if any, effect on the accuracy of the reflectance reading.

In a second embodiment, the shroud which includes an elongated housing assembly is pivotally mounted at its trailing end to the vehicle. The aperture housing is fixed to the shroud and is positioned between the marker and the source and receptor. In order to maintain a uniform light path length during measurement, that portion of the shroud which will overlie the marker when light is reflected back to the receptor is independently suspended and supported at a preselected and uniform distance from the road surface.

The geometric considerations governing each of the foregoing embodiments is discussed hereinafter.

Further features of the invention pertain to the particular arrangement of the parts of the vehicle apparatus whereby the above-outlined and additional operating features thereof are attained.

BRIEF DESCRIPTION OF THE DRAWINGS

FIG. 1 is a perspective view showing a van equipped with the present invention including a testing shroud mounted to the driver's side of the van;

FIG. 2 is a fragmentary side elevational and partial sectional view of the shroud assembly and shows a floating aperture assembly in a retracted or raised position;

FIG. 3 is a view similar to FIG. 2, showing the floating aperture assembly in an extended or lowered operating position;

DESCRIPTION OF THE PREFERRED EMBODIMENT

The Floating Aperture Embodiment

Figure 4:
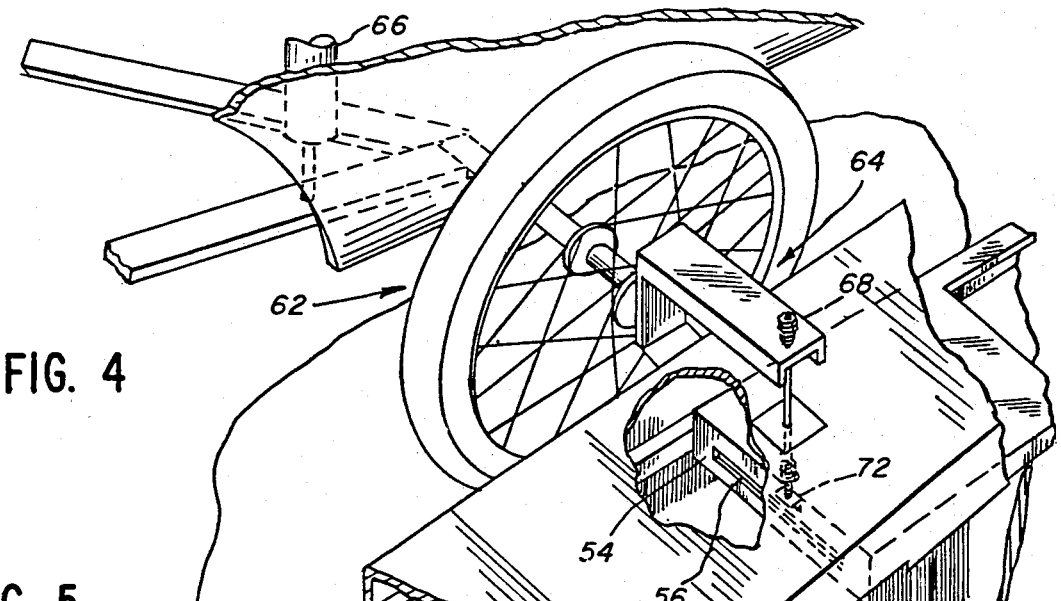
FIG. 4 is a fragmentary and partial perspective view showing the front end of the shroud and the floating aperture assembly.

Referring now to FIG. 1, the mobile testing apparatus 10 generally includes a van or other vehicle 12, having an elongated shroud assembly 14 mounted on the driver's side and a guide assembly 16 mounted to the front end of the van 12. The van 12 is a commercially available model which has been modified to carry the guide assembly 16 and the shroud assembly 14. The van 12 also is provided with data processing equipment 20 of a type known to those skilled in the art to receive and analyze data from the shroud assembly 14.

The van is shown on a roadway 18 on which a series of reflective pavement markers 22, 24, 26, 28 and 30 have been mounted as lane markers. The pavement markers illustrated may be of the type shown in Heenan, U.S. Pat. No. 3,332,327. However, as discussed herein, the invention is capable of use with reflective striping or other types of markers, and the word marker as used herein is used in the generic sense to mean a reflective item positioned in or on the roadway surface.

The guide assembly 16 is conventional and includes a boom-like arrangement 16a which is connected at one end to the front of the van and is supported at the forward end by a wheel 16b. A small pointer 16c is carried on the wheel and is aligned with the shroud assembly to permit the driver to align the shroud assembly over the markers by aligning the forwardly positioned pointer 16c over advance markers. Such conventional assemblies are used for guides in painting stripes on highways.

The shroud assembly 14 is an elongated, hollow, tubular body member 32 which in this embodiment is rigidly mounted to the van 12 and is inclined at an angle of six degrees to the horizontal, the leading edge 32a being lower than the trailing end 32b. In the illustrated embodiment, the shroud is 15 feet long, 9 inches high and 12 inches wide. A light-shielding curtain or brush assembly 34 is mounted to the leading edge 32a, and extends rearwardly therefrom toward the trailing end 32b and includes flexible brushes or a flexible curtain that extends between the shroud and the road surface to exclude ambient light. As the shroud 14 passes over a marker such as 26, the curtain or brushes 34 flex to permit the marker to enter the shroud.

A photometer assembly 36 is mounted in the trailing end 32b of the shroud and includes a light source 38 and a light receptor or photomultiplier tube 40. The controls for the light source 38 and the receptor 40 are connected to the data processing apparatus 20 by which data concerning reflected light intensity as a function of time is analyzed to identify whether the reflected light emanates from a marker and to determine peak intensity. The data processing apparatus may include conventional hardware and a CRT unit for display of data and instructions on diskettes.

Figure 6:
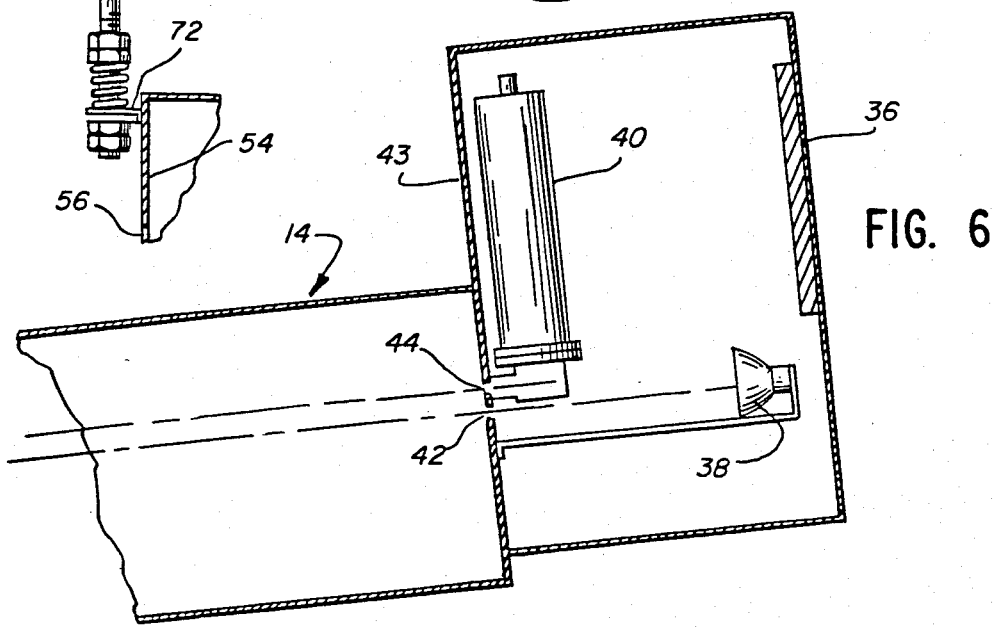
FIG. 6 is an enlarged sectional and elevational view of a photometer assembly mounted at the rear or trailing end of the shroud.

Referring to FIG. 6, the photometer assembly 36 is shown with the light source 38 and photomultiplier tube 40. The light from source 38 is directed into and along the length of the shroud 14 through a 0.280 inch square aperture 42 in the assembly wall 43, and reflected light returning from the marker through the shroud enters the assembly 36 through a 0.070 inch diameter aperture 44 in the assembly wall 43. The light source and photomultiplier tube are spaced from each other so as to provide a 0.2 degree observation angle relative to the reflective marker. That observation angle is a standard test point for reflective devices of many kinds.

To minimize changes in the length of the source/reflector/receptor light path, the shroud assembly also includes a floating aperture assembly, designated generally as 46. In accordance with the invention, the floating aperture assembly 46, in use, is maintained at a constant height from the roadway surface. The floating aperture assembly 46 includes a wedge-shaped housing 48 (FIG. 2) which is pivotally mounted at its trailing end to a lower edge of the bottom wall of the shroud at a pivot point 50. The housing 48 extends across the width of the shroud assembly 14, and includes a solid bottom surface 52, an upright wall 54 which has an open portion defining the floating aperture 56, and a top wall 58 which also defines a window 60 therein.

The leading end of the floating aperture assembly 46 is suspended from a fifth wheel assembly 62 (FIG. 4) by an adjustable bracket-rod-spring assembly 64. The fifth wheel is rotationally connected to the van's undercarriage and is movable by an air piston 66 between a retracted or storage position and an extended road-engaging position. The fifth wheel is raised and lowered by conventional type piston controls within the van 12. In the retracted position, the leading end of the floating aperture assembly 46 is in a raised and inactive position. In the extended and operative position, the fifth wheel 62 and suspension 64 maintain the aperture 56 at a predetermined distance from the roadway surface. Normally, the aperture 56 itself is only about 2.5 inches from the roadway surface.

Figure 5:
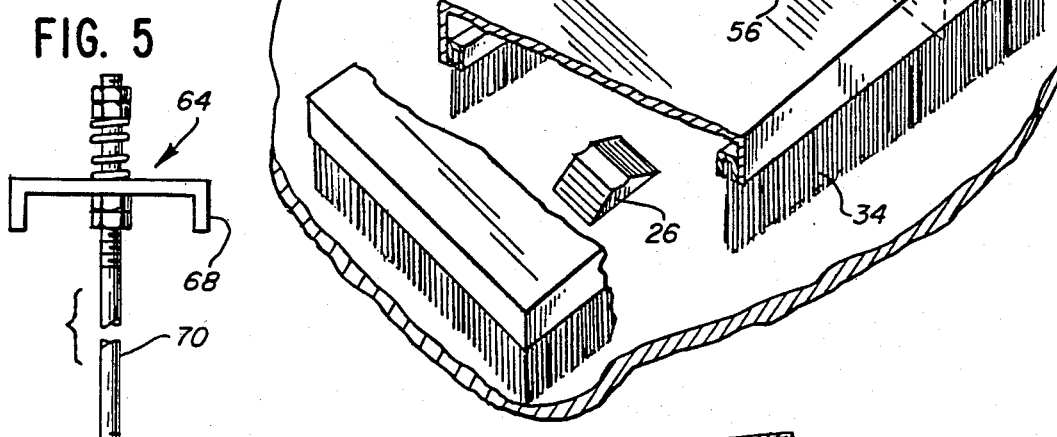
FIG. 5 is a fragmentary and side elevational view showing a suspension system for the floating aperture assembly.

Referring now to FIGS. 4 and 5, the wheel 62 and bracket 64 are shown in detail. The bracket 64 includes an angle iron 68 that is connected to the axle of the fifth wheel and extends over the center of the shroud assembly 14. A spring-biased and threaded suspension rod 70 extends from the angle iron 68 to a bracket 72 mounted to the leading end wall 54 of the housing 48. This mounting system maintains the aperture 56 at the desired controlled height, regardless of any vertical movement of the shroud assembly 14 with the van 12 due to bumps, etc. It should be noted that the leading end wall 54 of the aperture assembly 46 is forward of the trailing end of the curtain 34 so as to minimize ambient light effects on reflectivity readings.

Referring to FIG. 3, light from the source 38 travels along path 74, through the window 60 and aperture 56 until it strikes a marker such as 26. Light is then reflected from the front face of the marker with some returning through floating aperture 56 and window 60 along path 76 to the receptor 40.

Figure 7:
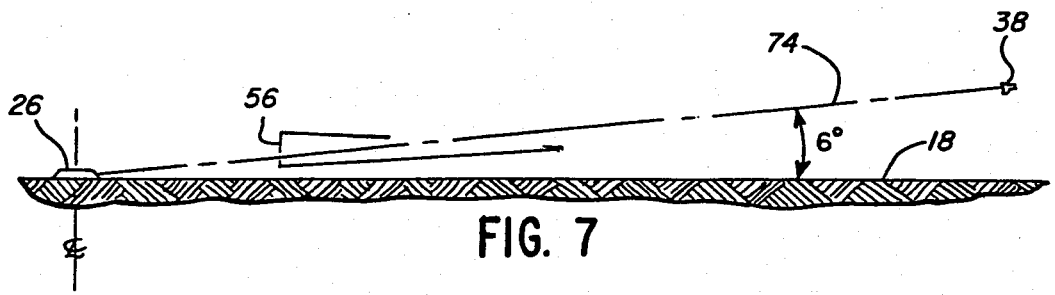
FIGS. 7, 8 and 9 are diagrammatic views showing the manner in which the floating aperture assembly cooperates in maintaining substantially uniform light path distances between the emitting and receiving elements of the photometer.
Figure 8:
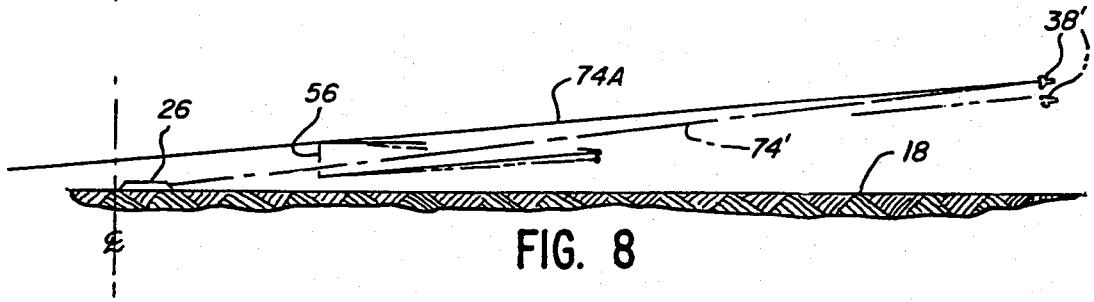
Figure 9:
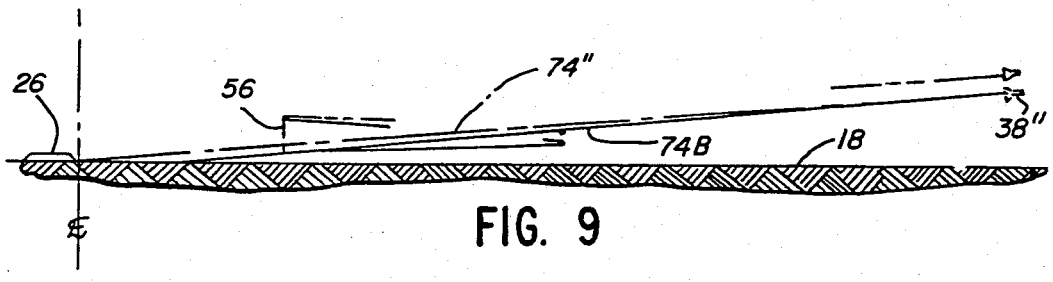

FIG. 7 shows the basic geometry of the system with light 74 traveling within the shroud and through the aperture assembly at a six degree angle to the road surface. However, if the van 12 bounces, the light source 38 may move vertically (e.g., 0.5 inch upwardly) as shown in FIG. 8 at 38'. The dark solid line 74a shows the light path still at six degrees, which light path will be longer than the path 74 of FIG. 7, and thus when the next marker is illuminated, there will be an erroneous measurement due to such lengthened path. By use of the floating aperture 56, a new light path 74' is established between the new position of light source 38', which light path is approximately equal in length to light path 74 of FIG. 7 and the marker thereby compensating for the changed height of the light source 38'. In a similar fashion, a decrease in the height of light source 38" (see FIG. 9) with respect to the roadway 18 without the use of floating aperture 56 would result in a shortened light path 74b which, when the marker is illuminated, would also result in an erroneous measurement due to a shortened light path. Allowing the floating aperture 56 to also track the roadway 18 establishes a light path 74" approximately equal to light path 74 of FIG. 7 and thereby produces a more accurate measurement of the marker.

By employing the floating aperture 56, changes in light path length due to movements in the light source and receptor position are minimized. This, in turn, permits very accurate calibration of the system and increased reliability in the results. In other words, erroneous readings due to changes in light path length are minimized.

As can be seen in this embodiment, the important concept is to maintain the aperture 56 fixed relative to the roadway and in this embodiment that is accomplished by providing an assembly which is independently suspended from a fifth wheel.

In operation, the van 12 with the fifth wheel 62 in the raised position is brought to the test site. The fifth wheel is lowered, the equipment (i.e., photometer, light source, computer, etc.) are energized and the ambient light is set to zero (0). A reference standard is set on the pavement and the operator moves the shroud over the standard. The output of the photomultiplier 40 corresponding to the standard is displayed on a cathode ray tube (not shown). Thereafter, the van 12 can be driven along the highway and the reflectance of each marker 22, 24, etc., measured and compared to the standard value. The photomultiplier output for each marker will be both digitally displayed and recorded together with the distance of the marker from a selected starting point so as to precisely identify and locate each tested marker. An audible signal will inform the driver that a marker has been recognized. Vehicle speed has no effect on testing, but the vehicle will normally be operated at between 30 and 50 mph during testing.

THE FLOATING SHROUD EMBODIMENT

In the first embodiment as previously described, the shroud is rigidly connected to the van or vehicle and the length of the light path is controlled by providing a floating aperture housing which during operation is maintained at a uniform and preselected distance from the roadway surface.

In the second embodiment as described hereinafter, the length of the light path is controlled by pivotally connecting the trailing end of the shroud to the van, fixing the aperture in relation to the shroud and maintaining the distance between the portion of the shroud which is expected to overlie the marker and the highway at a uniform and preselected distance.

Figure 10:
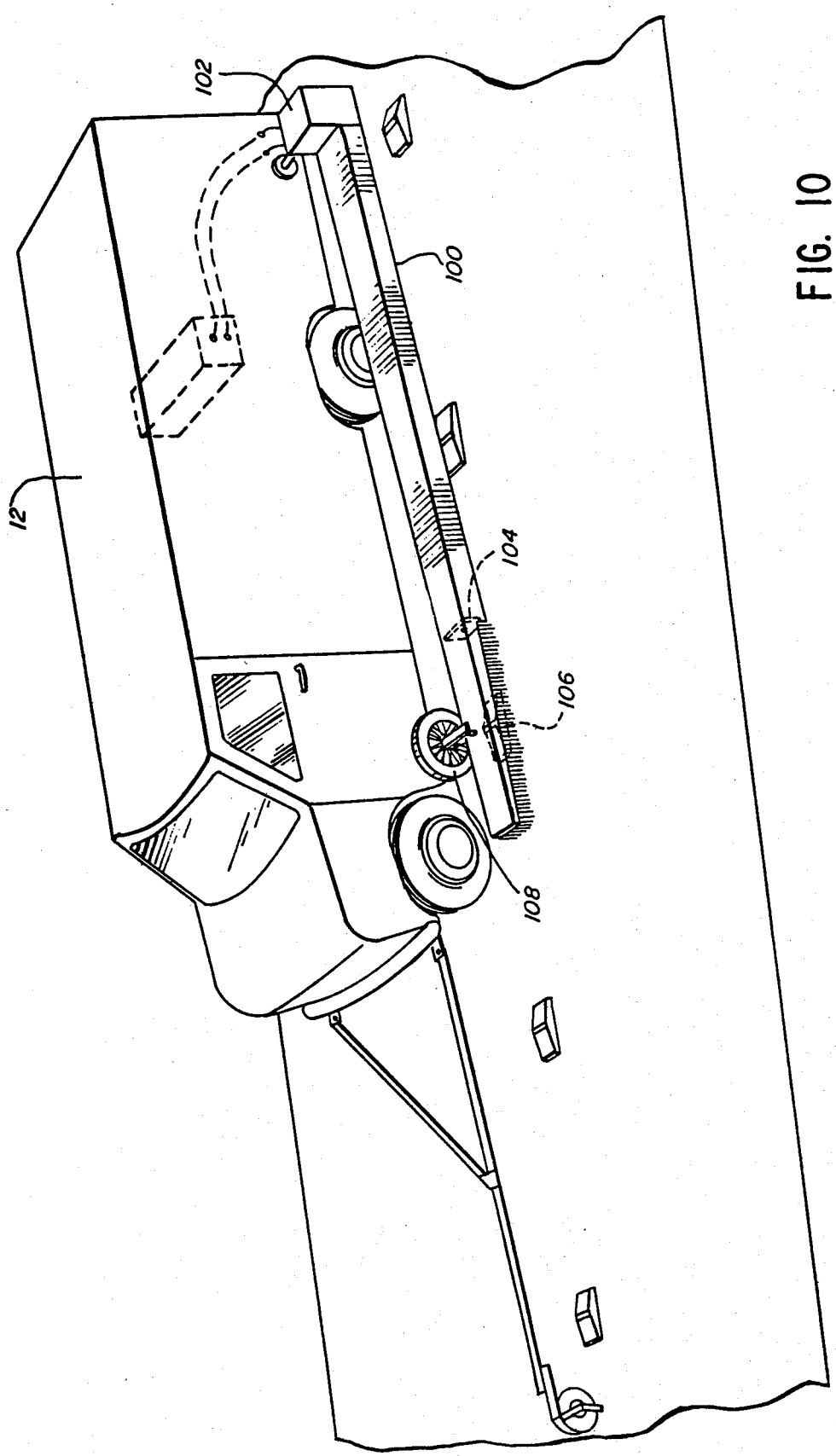
FIG. 10 is a perspective view showing a van with a pivotally mounted shroud assembly and in which the portion of the shroud which is intended to overlie the marker is positioned at a fixed distance from the road.

Referring now to FIG. 10, there is shown a van 12, like that shown in FIG. 1, and a shroud 100 similar to the shroud shown in FIG. 1. The shroud 100 is elongated and includes a photometer assembly 102 that includes the light source and light receptor. The light path is nominally fixed at six degrees to the road surface. A wall 104 with a light transmitting aperture is provided intermediate the photometer assembly and the road surface. In this embodiment the aperture is fixed relative to the shroud. In the nominal position, light from the source would be expected to strike the roadway at point 106, and if a marker were at that position, light would reflect back through the aperture housing to the receptor.

As described above, road conditions can cause the van to bounce and the light source may move upwardly or downwardly which can cause the light path to become longer or shorter.

In order to maintain a uniform light path regardless of upward or downward movement, the shroud is pivotally connected to the van at the trailing end and adjacent the photometer assembly 102 so that the shroud can pivot about a substantially horizontal axis. The portion of the shroud directly above the nominal contact point 106 is supported by retractable positioning means, such as a fifth wheel 108 which supports the shroud at that point and at a controlled, uniform and preselected height from the roadway surface. The combination of the pivotal connection, fixed aperture and contact point support provide a uniform light path, notwithstanding bouncing of the vehicle.

In FIG. 10, the van 12 is shown in the operating mode with the positioning means 108, which is a fifth wheel assembly similar to that shown in FIGS. 1-6, extended so as to contact the ground and support the shroud. It is understood that the positioning means can be retracted, so as to raise the shroud when transporting the apparatus to another test location.

Figure 11:
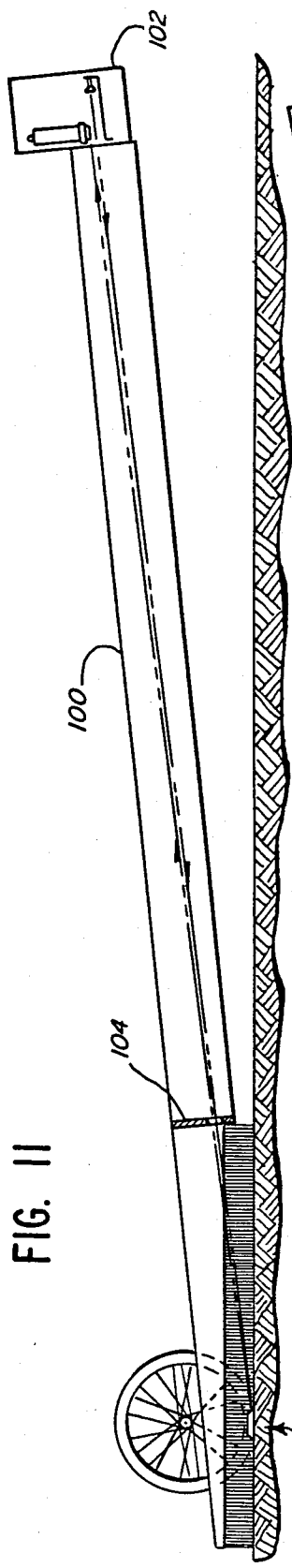
FIGS. 11, 12 and 13 are diagrammatic views showing the light path geometry when the shroud is in each of the expected, raised and lowered positions.
Figure 12:
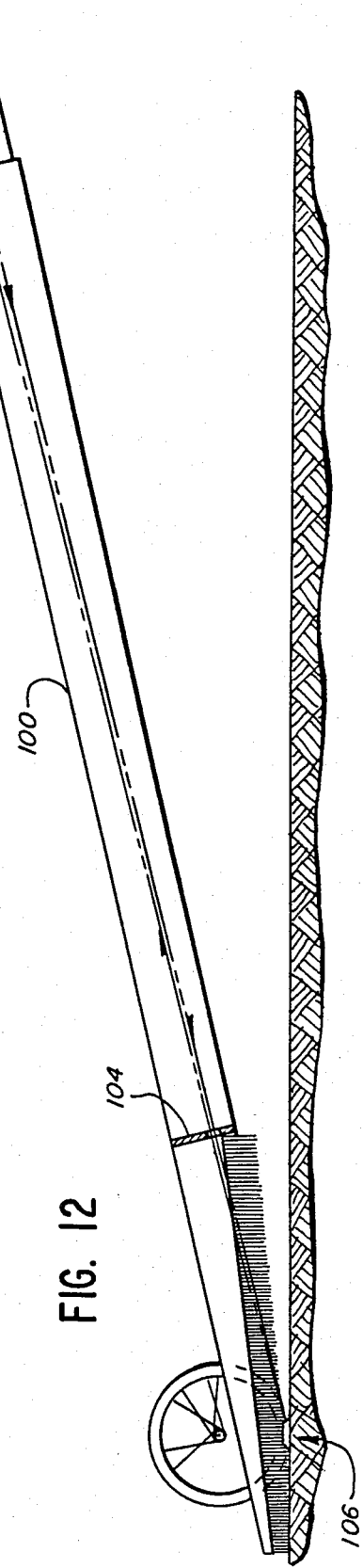
Figure 13:
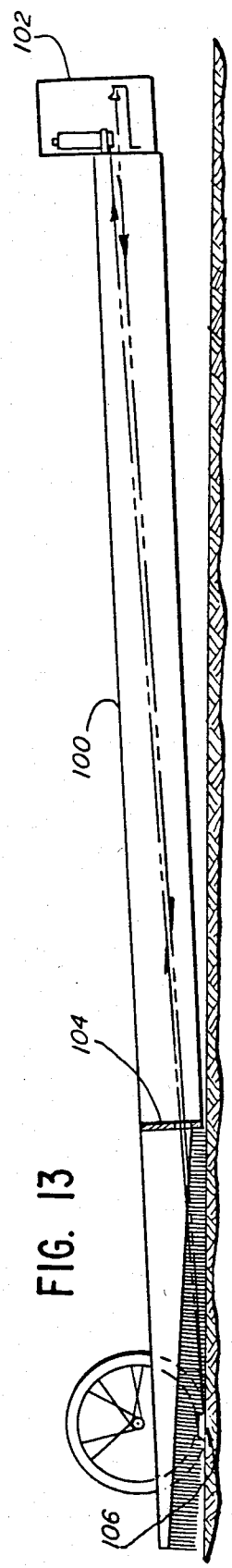

FIGS. 11, 12 and 13 diagrammatically show the light path geometry involved with this shroud construction. In FIG. 11, the shroud is shown with the light source and receptor assembly 102 and wall 104 and aperture are fixed in place. In this arrangement, the light beam is at six degrees to the roadway surface and strikes a marker as shown. The light then reflects back to the receptor. In this arrangement the trailing end of the shroud is pivotally connected to the van and the leading end is suspended by the fifth wheel positioning means. As can be seen, the positioning means is aligned with the nominal or expected contact point 106.

In the event the van bounces upwardly, the light source 102 moves upwardly as shown in FIG. 12. However, the height of the shroud at the nominal contact point remains the same. Furthermore, the wall 104 remains in the same relationship to the light source as in FIG. 11. This arrangement results in the new light path, although at a different angle which is of the same length as the light path in FIG. 11.

Furthermore, the position of the shroud may even drop due to uneven road surfaces. This would result in a downward movement of the light source as shown in FIG. 13. However, again due to the fixed aperture and floating front end, the light path length remains the same.

Thus this construction provides another embodiment whereby errors in reflectivity due to changes in light path caused by variations in a roadway surface are minimized.

It is understood that the reflectivity is determined in the same manner using data processing equipment as was the case in the previously described floating aperture embodiment.

While there has been described what is at present considered to be the preferred embodiments of the invention, it will be understood that various modifications may be made therein, and it is intended to cover in the appended claims all such modifications as fall within the true spirit and scope of the invention.

What is claimed is:

1. A mobile testing apparatus for continuous onsite reflective testing of markers on a roadway, comprising:
    an elongated shroud assembly constructed for mounting to an associated vehicle, said shroud assembly constructed to be aligned with the direction of movement of the associated supporting vehicle and generally adjacent a road surface, said shroud assembly including an elongated housing having a leading end and a trailing end; an incident light source and reflected-light receptor mounted to the trailing end of said shroud assembly for directing light to a marker through said shroud assembly and for receiving reflected light therefrom for analysis;
    an aperture housing which includes means defining a floating aperture mounted to said shroud assembly intermediate the leading and trailing ends, and through which incident light is directed to the marker and reflected light returns to said receptor; and
    positioning means for sensing the roadway surface and substantially continuously positioning said aperture housing and said floating aperture at a constant distance relative to said roadway surface, whereby said aperture remains substantially uniformly positioned relative to the roadway surface if said light source and receptor move vertically, and whereby the light path distance relative to the marker being tested remains substantially uniform.

2. Mobile testing apparatus as in claim 1, wherein said shroud assembly is a boxlike member, the interior of which is maintained substantially free of ambient light so that only light reflected from the marker is measured by the receptor.

3. Mobile testing apparatus as in claim 1, where said light source and said receptor are mounted in a photometer assembly and housing, said housing having a first aperture through which light from the source is directed to the reflective marker and a second aperture through which light from the reflective marker is received by the receptor.

4. Mobile testing apparatus as in claim 3, wherein the angle between the incident beam from the source and the reflected beam received by the receptor is fixed to about 0.2 degrees.

5. Mobile testing apparatus as in claim 1, further including data processing means operatively associated with said source and receptor for continuously receiving data from the reflected beam for measuring and recording reflectance of each of the markers tested.

6. Mobile testing apparatus as in claim 1, wherein said shroud assembly is a hollow tubular member having an elongated floating aperture housing in the bottom surface intermediate said shroud assembly ends, said floating housing having an aperture and a window therein to permit light to pass from said source to the marker and back to the receptor, said floating housing being mounted for controlled positioning relative to said roadway surface.

7. Mobile testing apparatus as in claim 6, wherein there is provided a fifth wheel rotationally positioned on said vehicle, with said floating housing being suspended from said fifth wheel, said fifth wheel being movable between a road-engaging position and a retracted position whereby when said fifth wheel is in the road-engaging position the distance between the roadway surface and floating aperture housing is controlled independent of vertical movement of said shroud assembly and when in the retracted position the floating aperture housing is moved upwardly from the roadway surface.

8. Mobile testing apparatus as in claim 7, wherein said floating aperture housing is wedge shaped and said aperture is provided in the front wall and said window in an upper wall of said housing.

9. Mobile testing apparatus as in claim 1, wherein there is further provided by light-excluding means mounted to the leading end of said shroud assembly and extending between said shroud assembly and the road surface for substantially preventing ambient light entering beneath the shroud.

10. Mobile testing apparatus as in claim 9, wherein said light excluding means extend from the leading end of said shroud assembly to a point on said shroud assembly rearwardly of the floating aperture so as to minimize ambient light entering the shroud assembly.

11. Mobile testing apparatus as set forth in claim 9, wherein said light-excluding means comprises flexible brushes suspended from said shroud assembly, said brushes permitting said shroud assembly to move over the marker being tested while both minimizing vertical movement of said shroud assembly and excluding ambient light.

12. An apparatus for mounting on a mobile frame for detecting reflectivity of markers on a roadway, said apparatus including a light source and a light receptor mounted on the apparatus for emitting and detecting reflected light as said apparatus moves along the roadway surface, said apparatus also including:
    means for controlling the length of the light path to maintain a substantially equal path length relative to the marker being tested regardless of the vertical movement of the source;
    said light path controlling means defining an aperture positioned between the source and the target marker through which incident and reflected light must pass; and
    positioning means for maintaining said aperture at a preselected height from the roadway surface regardless of vertical movement of the light source and receptor.

13. A mobile testing apparatus for continuous onsite testing of reflective markers on a roadway comprising:
an elongated shroud assembly constructed to be mounted to a vehicle in alignment with the direction of movement of the vehicle and positioned generally adjacent a road surface and to pass over a marker located in the roadway;
said shroud assembly including an elongated housing having a leading end and a trailing end; an incident-light source and a reflected-light receptor mounted adjacent the trailing end for directing light to a roadway marker through said shroud assembly and for receiving reflected light therefrom for analysis;
said housing also including means defining an aperture intermediate the leading and trailing ends and through which incident light is directed to the marker and reflected light is returned to said receptor;
wherein there is further provided means for pivotally mounting the shroud assembly at the trailing end thereof to said vehicle; said aperture means being fixed relative to said shroud, light source and receptor; and means for uniformly spacing from said roadway surface, the portion of the shroud expected to overlie the marker at time of the reflectivity measurement;
whereby the length of the light path from the source to the marker and back to the receptor is substantially constant, notwithstanding movement of the light source relative to the roadway.

14. A mobile testing apparatus as in claim 13, wherein the overlying point is that point on the shroud which will be directly above the marker when light from the source strikes the marker.

15. A mobile testing apparatus as in claim 13, wherein said spacing apparatus is retractable between a supporting and a non-supporting position.

16. A mobile testing apparatus as in claim 15, wherein said spacing apparatus includes a fifth wheel mounted to said vehicle adapted to engage said roadway and adapted to uniformly support said housing at said overlying point from said roadway.

* * * * *